US011642315B2

(12) United States Patent
Di Renzo et al.

(10) Patent No.: US 11,642,315 B2
(45) Date of Patent: *May 9, 2023

(54) METHOD FOR PREPARING A PHARMACEUTICAL PRODUCT

(71) Applicant: NOVARTIS AG, Basel (CH)

(72) Inventors: Elodia Di Renzo, Basel (CH); David Hook, Rheinfelden (CH); Markus Krumme, Allschwil (CH); Steffen Lang, Reinach (CH); Massimo Moratto, Basel (CH); Joerg Ogorka, Reinach (CH); Jim Parks, Belmont, CA (US); Dale Ploeger, Menlo Park, CA (US); Norbert Rasenack, Weil am Rhein (DE); Hendrik Schneider, Basel (CH); Stefan Steigmiller, Freiburg (DE); Gordon Stout, El Cerrito, CA (US); Patrick Tritschler, Freiburg (DE); Fabian Weber, Freiburg (DE)

(73) Assignee: Novartis AG, Basel (CH)

( * ) Notice: Subject to any disclaimer, the term of this patent is extended or adjusted under 35 U.S.C. 154(b) by 377 days.

This patent is subject to a terminal disclaimer.

(21) Appl. No.: 16/652,097

(22) PCT Filed: Sep. 28, 2018

(86) PCT No.: PCT/IB2018/057541
§ 371 (c)(1),
(2) Date: Mar. 30, 2020

(87) PCT Pub. No.: WO2019/069195
PCT Pub. Date: Apr. 11, 2019

(65) Prior Publication Data
US 2020/0315973 A1     Oct. 8, 2020

Related U.S. Application Data

(60) Provisional application No. 62/566,563, filed on Oct. 2, 2017.

(30) Foreign Application Priority Data

Feb. 1, 2018  (EP) .................................... 18154680

(51) Int. Cl.
*A61K 9/48* (2006.01)
*A61J 3/07* (2006.01)
*A61K 9/00* (2006.01)

(52) U.S. Cl.
CPC ............. *A61K 9/4833* (2013.01); *A61J 3/074* (2013.01); *A61K 9/0053* (2013.01)

(58) Field of Classification Search
None
See application file for complete search history.

(56) References Cited

U.S. PATENT DOCUMENTS

| | | | | |
|---|---|---|---|---|
| 4,431,070 A | * | 2/1984 | Andrews | G01G 13/16 |
| | | | | 177/DIG. 5 |
| 5,826,633 A | * | 10/1998 | Parks | B65B 1/366 |
| | | | | 141/237 |
| 8,545,878 B1 | | 10/2013 | Kee et al. | |
| 8,783,305 B2 | | 7/2014 | Naydo et al. | |
| 2007/0179196 A1 | * | 8/2007 | Han | A61P 43/00 |
| | | | | 514/530 |
| 2013/0118638 A1 | * | 5/2013 | Hopkins | B65B 1/04 |
| | | | | 141/234 |
| 2022/0175682 A1 | * | 6/2022 | Bieri | C07D 487/04 |

FOREIGN PATENT DOCUMENTS

| | | | | |
|---|---|---|---|---|
| BE | 1010353 A5 | * | 6/1998 | ............... A61J 3/00 |
| GB | 2066662 A | | 7/1981 | |
| WO | 2013090841 A2 | | 6/2013 | |
| WO | 2013111105 A1 | | 8/2013 | |
| WO | 2016151500 A1 | | 9/2016 | |
| WO | 2016205270 A1 | | 12/2016 | |

OTHER PUBLICATIONS

Ha Phan et al., "Characterization of the properties of powder excipients commonly used in pharmaceutical compounding", Particulate Science and Technology, vol. 34, No. 3, May 3, 2016, pp. 271-277.
T. Freeman et al. "Capsule Filling Performance of Powdered Formulations in Relation to Flow Characteristics", "Particulate Materials", Royal Society of Chemistry, pp. 131-136, Jan. 1, 2011.
Juan G. Osorio et al. "Effects of powder flow properties on capsule filling weight uniformity", Drug Development and Industrial Pharmacy, vol. 39, No. 9, Sep. 11, 2013, pp. 1464-1475.
Faulhammer, Process understanding and optimization of dosing and filling systems for the production of pharmaceutical hard capsules, Doctoral Thesis, Apr. 2015, 1-168.

(Continued)

*Primary Examiner* — Aradhana Sasan
(74) *Attorney, Agent, or Firm* — Emily T. Wu

(57) ABSTRACT

A method of preparing a pharmaceutical product comprises the steps of (a) providing a neat active pharmaceutical ingredient (API) complying with at least five of the following parameters determined by using a FT4 powder rheometer: (i) specific basic flow energy of at most 60 mJ/g; (ii) stability index of 0.75 to 1.25; (iii) specific energy of at most 10 mJ/g; (iv) major principle stress at 15 kPa of at most 40; (v) flow function at 15 kPa of at least 1.3; (vi) consolidated bulk density at 15 kPa of at least 0.26 g/mL; (vii) compressibility of at most 47%; and (viii) wall friction angle of at most 40°; (b) dispensing the neat API of step (a) into a bottom part of a pharmaceutical carrier using a vacuum assisted metering and filling device; and (c) encapsulating the bottom part, thereby producing a pharmaceutical product.

15 Claims, 4 Drawing Sheets

(56) References Cited

OTHER PUBLICATIONS

Qiao, et al., Chinese Medicine, Pharmacy of Traditional Chinese Medicine, Encyclopedia of Chinese Medicine, Apr. 2017, with machine English translation.

Liang et al, Pharmaceutical Textbooks for the Fourth Round of planning in National Medical Colleges and Universities, China Pharmaceutical Science and Technology Press, Mar. 2016, 388-390.

Zhu et al, Pharmaceutics of Traditional Chinese Medicine, China Agricultural University Press, May 2015, 183-184.

Guerin et al, Rheological characterization of pharmaceutical powders using tap testing, shear cell and mercury porosimeter, International Journal of Pharmaceutics, 1999, 189, 91-103.

* cited by examiner

METHOD FOR PREPARING A PHARMACEUTICAL PRODUCT

The present invention relates to methods of preparing pharmaceutical products, involving filling active pharmaceutical ingredient powders into pharmaceutical carriers with a vacuum assisted metering and filling device. The methods disclosed herein can be used in a continuous process, such as in a high-throughput process for producing a pharmaceutical product.

BACKGROUND OF THE INVENTION

Formulating an active pharmaceutical ingredient (API) from its discovery through early clinical phases until late clinical phases and a final commercial product is demanding and resource intensive. The commercial formulation containing the API and the related manufacturing process generally comprises excipients blending or granulation. Geometric dilution, wet granulation and dry blending are applied especially in the manufacturing of low-dose formulations. A lot of effort is spent about achieving an adequate mixing method to ensure uniformity of dosage and homogeneity between excipients and API. Furthermore lot of effort is addressed on scale-up operations and re-formulation occurs whenever an early phase (or first approach) formulation showed an unexpected biopharmaceutical profile or turns out as not adequate for the late phase processing. To accelerate development, APIs can be dosed neat into capsules in the early phase. Pepper pot dosing principle combined with classical weighing (Xcelodose®) is a widely used solution. However, in the later phases, a classical formulation with excipients is still developed.

By using neat API in capsule, formulation development time can be reduced by simply evaluating the compatibility between the capsule shell and the API, instead of investigating excipient compatibility and fully formulating a dosage form. Analytical method development time can also be reduced because no specificity needs to be qualified, as no interfering excipients are present. Thus, the analytical method for the drug substance can suffice for the drug product. However there are challenges to achieving neat API filling into capsules with consistent fill, especially with low fill weights.

SUMMARY OF THE INVENTION

The present invention relates to an engineering and manufacturing concept with the aim of direct encapsulation of neat API (or API with a very low amount of additives) in a very wide dose range, through the entire development pathway of the drug product, until the commercial manufacturing. The method of the present disclosure is particularly useful in a continuous process, such as in a high-throughput process for producing a pharmaceutical product.

The method of the present disclosure has the unique capacity to accommodate an unusually wide range of powder properties, including powders that cannot be filled in any other equipment, enabling the user of the platform to cope with the peculiarities of neat API powders (e.g. an excess of cohesion, adhesion, bad flow etc.). The disclosed method is capable of coping with a multitude of complex aspects of the drug development, in a relatively simple ensemble of technologies and organizational solutions which radically simplify the development and manufacturing of oral pharmaceutical forms. The method can be employed recursively for any new API that is entering the development pathway of the pharmaceutical research and development (wherein intrinsic solubility characteristics are sufficiently favorable), until the commercial manufacturing.

To implement the above-described aims, the method of the present disclosure applies an uncommon ensemble of equipment and technologies as well as novel procedures for the understanding, prediction, selection, modification and control of powder behavior.

Accordingly, the present invention provides a method of preparing a pharmaceutical product, comprising the steps of:
(a) providing an active pharmaceutical ingredient (API) which complies with at least five of the following parameters (i)-(viii) as determined by using a FT4 powder rheometer:
  (i) specific basic flow energy (sBFE) of at most 60 mJ/g;
  (ii) stability index (SI) of 0.75 to 1.25;
  (iii) specific energy (SE) of at most 10 mJ/g;
  (iv) major principle stress at 15 kPa (MPS-15) of at most 40;
  (v) flow function at 15 kPa (FF-15) of at least 1.3;
  (vi) consolidated bulk density at 15 kPa (CBD-15) of at least 0.26 g/mL;
  (vii) compressibility of at most 47%; and
  (viii) wall friction angle (WFA) of at most 40°;
(b) dispensing the API of step (a) into a bottom part of a pharmaceutical carrier using a vacuum assisted metering and filling device; and
(c) encapsulating the bottom part of said pharmaceutical carrier with a complementary lid part of said pharmaceutical carrier, thereby producing a pharmaceutical product.

In a related aspect the present invention provides a method for filling a pharmaceutical carrier or dosage form with a neat active pharmaceutical ingredient (API) powder, which method comprises,
(a) dispensing the API powder into a bottom part of the pharmaceutical carrier or dosage form using a vacuum assisted metering and filling device; and
(b) encapsulating the bottom part of said pharmaceutical carrier or dosage form with a complementary lid part of said pharmaceutical carrier or dosage form, thereby producing a filled pharmaceutical carrier or dosage form;
wherein the neat API complies with at least five of the following parameters (i)-(viii) as determined by using a FT4 powder rheometer:
  (i) specific basic flow energy (sBFE) of at most 60 mJ/g;
  (ii) stability index (SI) of 0.75 to 1.25;
  (iii) specific energy (SE) of at most 10 mJ/g;
  (iv) major principle stress at 15 kPa (MPS-15) of at most 40;
  (v) flow function at 15 kPa (FF-15) of at least 1.3;
  (vi) consolidated bulk density at 15 kPa (CBD-15) of at least 0.26 g/mL;
  (vii) compressibility of at most 47%; and
  (viii) wall friction angle (WFA) of at most 40°.

Thus the pharmaceutical carrier/dosage form once filled and sealed typically contains only neat API (noting that the neat API may include no more than 5%, 4%, 3%, 2%, 1%, 0.5% or 0.1% in additives).

The present invention also provides a pharmaceutical carrier/dosage form, such as an oral dosage form, containing only neat API (noting that the neat API may include no more than 5%, 4%, 3%, 2%, 1%, 0.5% or 0.1% in additives), obtained or obtainable by the process of the invention described in any of the embodiments herein.

The present inventors have developed a method to predict whether an API is suitable for being formulated directly as neat API in a pharmaceutical product, or does requires further improvement (particle engineering). Accordingly, step (a) represents a quality check defining a new minimum standard of certain powder parameters required for formulating an API as a neat API in a pharmaceutical product.

The present invention therefore also provides a method for predicting whether an API is suitable for being formulated directly as neat API in a pharmaceutical product, which method comprises determining using a FT4 powder rheometer whether the API complies with at least five of the following parameters (i)-(viii) as determined by using a FT4 powder rheometer:
  (i) specific basic flow energy (sBFE) of at most 60 mJ/g;
  (ii) stability index (SI) of 0.75 to 1.25;
  (iii) specific energy (SE) of at most 10 mJ/g;
  (iv) major principle stress at 15 kPa (MPS-15) of at most 40;
  (v) flow function at 15 kPa (FF-15) of at least 1.3;
  (vi) consolidated bulk density at 15 kPa (CBD-15) of at least 0.26 g/mL;
  (vii) compressibility of at most 47%; and
  (viii) wall friction angle (WFA) of at most 40°.

While the use of a vacuum assisted metering and filling device such as the drum filler technology has been described previously in the pharmaceutical industry in relation to inhalation products containing excipients (such as lactose blends or engineered particles, for example Pulmo-Spheres™), its application for dosage forms manufactured using neat API, including oral dosage forms is seen as unique. More common in the industry is to dose formulated blends or granulated material into a capsule using dosator or tamping pin filling principles.

In further described embodiments, the vacuum drum dispenser comprises a powder trough equipped with a fluidization device, in particular an acoustic transducer, more specifically an ultrasonic transducer. In addition, the API may be consolidated in the bottom part of the pharmaceutical carrier by vibration, shaking or tapping prior to step (c).

In a particular embodiment, the pharmaceutical product is an oral dosage form. An example of an oral dosage form is the injection-molded, tablet shaped carrier described in the embodiment below and elsewhere in the specification.

In one embodiment, the pharmaceutical carrier in step (c) is a tablet shaped carrier (also referred to herein as Prescido™) as a novel pharmaceutical dosage form. This carrier is designed to have the functionality of a standard pharmaceutical capsule while maintaining the patient appeal of a tablet. The carriers described herein are manufactured via a precision injection molding process, using a formulation designed to perform well in thermal processes. The high performance of the formulation in the injection molding process enables flexibility in design of the carriers allowing for robust manufacture of design features with very small dimensions—traditionally a challenge in injection molding. Design & manufacturing features together with their benefits include, inter alia, thin wall sections (fast carrier disintegration times in aqueous media), small snap close features (tight closure prevents opening of carrier during transport and limits tampering of carrier contents), numbering of cavities (traceability and sorting of parts before use) and high weight & dimension precision (robust handling processes).

In addition to facile thermal processing properties, the formulation developed imparts a number of benefits to the carriers compared to traditional capsules, such as, for example, low water content (improved compatibility with water sensitive actives), low moisture absorption and sensitivity at standard manufacturing conditions, and comparably fast dissolution (rapid carrier rupture in aqueous media).

Thus, Prescido™ carriers have an advantage over traditional capsules due to having favorable water content & sorption properties, an advantage for processing and stability of water sensitive compounds.

DETAILED DESCRIPTION OF THE PREFERRED EMBODIMENTS

The present invention provides a method of preparing a pharmaceutical product, comprising the steps of:
  (a) providing an active pharmaceutical ingredient (API) which complies with at least five of the following parameters (i)-(viii) as determined by using a FT4 powder rheometer:
    (i) specific basic flow energy (sBFE) of at most 60 mJ/g;
    (ii) stability index (SI) of 0.75 to 1.25;
    (iii) specific energy (SE) of at most 10 mJ/g;
    (iv) major principle stress at 15 kPa (MPS-15) of at most 40;
    (v) flow function at 15 kPa (FF-15) of at least 1.3;
    (vi) consolidated bulk density at 15 kPa (CBD-15) of at least 0.26 g/mL;
    (vii) compressibility of at most 47%; and
    (viii) wall friction angle (WFA) of at most 40°;
  (b) dispensing the API of step (a) into a bottom part of a pharmaceutical carrier using a vacuum assisted metering and filling device; and
  (c) encapsulating the bottom part of said pharmaceutical carrier with a complementary lid part of said pharmaceutical carrier, thereby producing a pharmaceutical product; as further defined in the claims.

Figure 2:
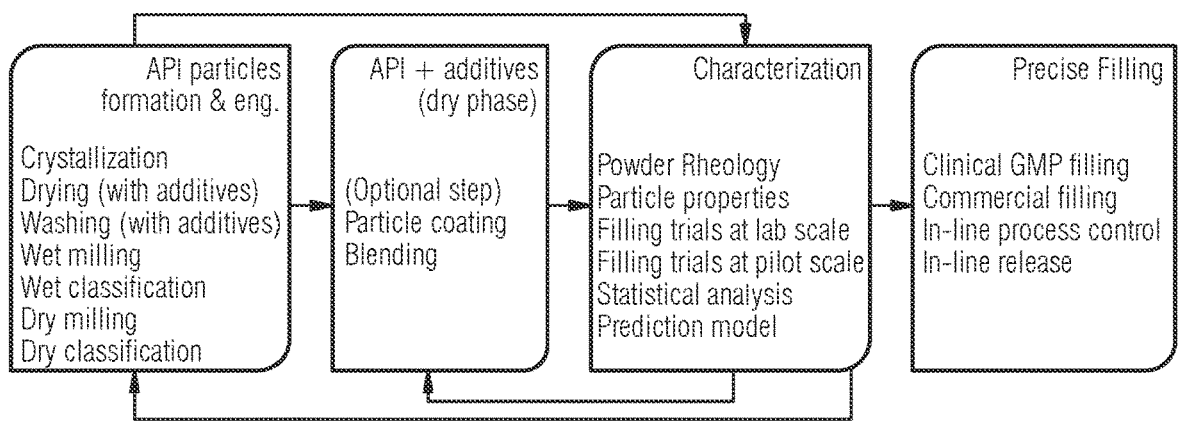
FIG. 2 shows a flowchart of the steps involved in a method of preparing a pharmaceutical product.

A flow chart of the method disclosed herein, valid at any scale, is provided in FIG. 2.

Neat API Selection and Modification

We have developed an '8-parameter model' capable of distinguishing and predicting filling behavior of powders. The eight parameters are:

sBFE: Specific Basic Flow Energy (mJ/g): obtained from BFE (obtained from standard FT4 test platform) divided by the split mass of the sample SI: Stability Index, standard variable, dimensionless SE: Specific Energy (mJ/g), standard variable MPS @ 15 kPa: major Principal Stress, standard variable FF @ 15 kPa: Flow function (dimensionless), from shear cell, standard variable CBD @ 15 kPa: Consolidated Bulk Density (g/mL), standard variable (from shear cell)
CPS: Compressibility (%), standard variable
WFA: Wall Friction Angle (degree°), standard variable The table below shows the ranges, and preferred ranges for each parameter that form part of the model. Each range, preferred and most preferred, for each parameter can be combined independently with each range, preferred and most preferred for any other parameter.

| Range\variable | sBFE | SI | SE | MPS-15 | FF-15 | CBD-15 | CPS | WFA |
|---|---|---|---|---|---|---|---|---|
| At most | <60 | 0.75-1.25 | <10 | <40 | >1.3 | >0.26 | <47% | <40° |
| More preferably at most | <25 | 0.83-1.18 | <8 | <33 | >3 | >0.45 | <35% | <34° |
| most preferably at most | <6 | 0.9-1.1 | <6 | <25 | >10 | >0.6 | 5-21% | <28° |

In preferred embodiments, the powder parameters in step (a) fulfil the following requirements, preferably at least five of the following requirement:
  (i) the sBFE is at most 25 mJ/g, in particular at most 6 mJ/g; and/or
  (ii) the SI is 0.83 to 1.18, in particular 0.9 to 1.1; and/or
  (iii) the SE is at most 8 mJ/g, in particular at most 6 mJ/g; and/or
  (iv) the MPS-15 is at most 33, in particular at most 25; and/or
  (v) the FF-15 is at least 3, in particular at least 10; and/or
  (vi) the CBD-15 is at least 0.45 g/mL, in particular at least 0.6 g/mL; and/or
  (vii) the compressibility is at most 35%, in particular 3-15%; and/or
  (viii) the WFA is at most 34°, in particular at most 28°.

A standard FT4 powder rheometer offers at least 6 powder characterization methods (per measurement cylinder diameter). Those selected for analysis are
  25 mm_1C_Split_Rep+VFR_R01;
  25 mm_Shear_15 kPa;
  25 mm_Compressibility_1-15 kPa;
  25 mm_Wall Friction_30 kPa.

The parameters can be divided into four groups based on these four selected characterization methods.
  Group 1—(i) sBFE; (ii) SI; (iii) SE
  Group 2—(iv) MPS-15; (v) FF-15; (vi) CBD-15
  Group 3—(vii) CPS
  Group 4—(viii) WFA.

FT4 powder rheometers are commercially available from Freeman Technology.

If four of the parameters are outside the indicated ranges, the powder is predicted as borderline in term of manufacturability. If more than four of the parameters are outside the indicated ranges, the powder is most probably and practically unworkable in any automatic machine here described as neat API. Moreover, it was found that if the MPS is very high, and in minor manner also the WFA is high, the powder is prone to build up in the filling and dosing device. This is a negative characteristic for sonic/ultrasonic filling technology. On the other hand, if the SI is too high, the powder changes its characteristics over time, rendering it more sensitive to shear force. Such a powder is less workable in the standard vacuum drum filling technology which uses a stirrer.

In a preferred embodiment, at least one of the parameters is selected from parameters (i) to (iii) and at least one of the parameters is selected from parameters (iv) to (vi)—i.e. at least one from Group 1 and at least one from Group 2. Preferably at least one of the Group 1 parameters is parameter (i) or (iii) and at least one of the Group 2 parameters is parameter (iv) or (v).

In another embodiment, which may be combined with the previous embodiment, at least one of the parameters is parameter (vii) or (viii)—i.e. Group 3 or Group 4.

Where the vacuum assisted metering and filling device is equipped with an ultrasonic device so to assist metering and dispensing of the API, it can be advantageous for the sBFE to be 29 or less, such as no more than 25. The CPS in this situation could be up to 65%.

In one embodiment the WFA is no more than 34 and/or the CPS is no more than 35.

Where the vacuum assisted metering and filling device is equipped with a stirrer so to assist metering and dispensing of the API, it can be advantageous for the SI to be 0.83 to 1.18, such as 0.9 to 1.1 and the CPS to be no more than 35%.

Thus the present invention also provides a method for predicting whether an API is suitable for being formulated directly as neat API in a pharmaceutical product using the 8 parameter model described above (all embodiments thereof).

Often, step (a) of the method will comprise a wet phase (FIG. 2, very left part), in which the neat API is produced. Commonly, such a wet phase comprises a crystallization step. This crystallization step can already be controlled in such a way that a desirable particle size of the crystals of the neat API is achieved. Parameters and means for controlling particle size in a crystallization process are well-known in the field, and include the settings of temperature, humidity, pH, agitation as well as the selection of suitable salts, buffers and organic solvents. Selection of these parameters vary for the API in question, and their determination forms part of the production process of the API. Following crystallization, the API is usually filtered and dried.

However, in further embodiments, step (a) of the method may further comprises wet milling of the API which will further reduce particle size.

Particle size may also be controlled by the addition of additives during the wet phase. Suitable additives are typically used as suspensions, solutions or as solids. The identity of the additive and the time-point during the process whereby said additive is added is specific to the API for which the process is being developed. Alternatively or in addition, additives may also be added to the API during wet phase to improve process performance or surface property benefits, such as better wettability.

The additives may be added at one or more time points during the manufacturing process, for example, during the crystallization step, during the filtration step, and/or during the drying step. For example, the API host particles can be coated with polymers in wet phase during crystallization or in suspension after crystallization or after milling.

The ratio of additive used is always low enough not to affect the API Content Uniformity nor the accuracy of mass sensor measuring. This is a concept in contrast to conventional formulation, where the API is always diluted within considerable amount of excipients especially for low doses. Accordingly, the amount of added additives is very low. For example, the one or more additive may be added during or after the crystallization step, filtration step, or drying step to an amount of at most 2% (w/w), preferably at most 1.5% (w/w), more preferably at most 1% (w/w), even more preferably at most 0.5% (w/w), and most preferably at most 0.1% (w/w). The one or more additive may be selected from the group consisting of hydroxypropyl cellulose, hydroxypropyl methylcellulose, polyvinyl pyrrolidone, acrylic polymers, sodium lauryl sulfate, gelatine, sugar esters such as sucrose monostearate and sucrose monopalmitate, and any combination thereof.

Following the wet phase, the API may optionally be further conditioned in a dry phase. For example, step (a) of the method may further comprises dry milling and/or sieving of the API. The sieving may be selected from sieving through conical sieving equipment, oscillating sieving, or screen sieving assisted by ultrasonic vibration.

Also in dry phase API particles may be processed and further coated with fine additives in the context of physical properties enhancement, in order to obtain process performance benefit (processing aid and surface property aid; see FIG. 2, middle left). Accordingly, in some embodiments, step (a) of the method further comprises a dry phase, in which one or more additive is added to an amount of at most 5% (w/w), preferably at most 4% (w/w), more preferably at most 3% (w/w), even more preferably at most 2% (w/w), and most preferably at most 1% (w/w.

The additive may be typically added after the isolation of the API in the wet phase, thereby being added directly prior to or as part of the dry phase API conditioning process. Established technologies available in commercial environment may be utilized. For example, the one or more additive is added by (i) low shear mixing, in particular in a tumbler mixer, (ii) high shear mixing, in particular in a rotary mixer, or (iii) very high shear mixing, in particular in a mechano-fusion. Mixing is typically conducted for a duration of at least 3 minutes and up to three hours.

During the dry phase, additives are typically used as solids. In certain embodiments, the one or more additive is selected from the group of hydrophobic colloidal silicon dioxide, hydrophilic colloidal silicon dioxide, magnesium stearate, stearic acid, sodium stearyl fumarate, poloxamer 188, hydrogenated vegetable oil, or any combination thereof.

The intention of the additives addition and their different processing methods in step (a) of the current process invention is in first instance to achieve a sufficient level of powder rheology characteristic.

In any case, the final neat API provided in step (a) comprises at most 5% (w/w) of an additive, preferably at most 4% (w/w), more preferably at most 3% (w/w), even more preferably at most 2% (w/w), and most preferably at most 1% (w/w).

As noted above, the skilled person knows how to adapt a powder parameter to comply with the requirements set out in step (a). In a parallel instance, additives may also be added within the indicated ranges in order to achieve an improvement in term or biopharmaceutical profile of the API. In addition, Scanning Electron Microscopy (SEM) gives a qualitative impression of particle size and shape. It can be used only as a visual guidance, as the small sample size may not be representative of the batch.

Neat API Filling into Capsules

In step (b) of the method the API of step (a) is dispensed into a bottom part of a pharmaceutical carrier using a vacuum assisted metering and filling device. Such a device allows dosing from below 0.25 mg up to half gram, delivering high precise dosing across the range. Thus, the method of the present disclosure allows to dose a total fill mass which can be as low as 0.25 mg with high precision, without any classical formulation step involved. The vacuum assisted metering and filling device allows filling of poor flowing and cohesive powders. During dose forming low mechanical stress is applied to the powder and the risk of adhesion to equipment surfaces is reduced with respect of other filling principles. These advantages provide a wider range of processable powder properties and a higher process robustness for encapsulation of neat drug substance compared to conventional technologies, which are traditionally used for large scale encapsulation of solid oral products.

Step (b) is only functional if the requirements of step (a) are met, for which reason steps (a) and (b) are interrelated. Accordingly, the present disclosure allows determining whether a powder can be dispensed and dosed using a vacuum assisted metering and filling device. At the same time, the present disclosure provides valuable guidance to the skilled person how a certain API must be (re-)configured to render it suitable for dispensing by a vacuum assisted metering and filling device.

While use of a vacuum assisted metering and filling device such as the drum filler technology is well known in the pharmaceutical industry with a focus on inhalation products, its application for oral dosage forms manufacturing using neat API is seen as unique. Accordingly, in a preferred embodiment, the pharmaceutical product is an oral dosage form. More common in the industry is to dose formulated blends or granulated material into a capsule using dosator or tamping pin filling principles.

The use of a vacuum assisted metering and filling device is of particular advantage, since it allows applying the method of the present disclosure in a continuous process. As a consequence, the method of the present invention can be used in a high-throughput process for producing a pharmaceutical product, allowing the production of 70,000 units/h or even more. As a result, the present method allows preparing a pharmaceutical product using neat API, i.e. an API comprising at most 5% (w/w) of an additive throughout all development stages of the pharmaceutical drug including its final commercial production. Prior art methods, which do not comprise steps (a) and (b) of the present method, exhibit a low throughput only. In order to achieve high-throughput production the API had to be (re-)formulated in a pharmaceutical composition during the various development stages.

In a preferred embodiment, the vacuum assisted metering and filling device is a rotatable drum. For example, the vacuum is applied into the drum cavity at −100 to −800 mBar, such as at −200 to −800 mBar, preferably −300 to −800 mBar, more preferably −400 to −800 mBar, such as at −500 to −800 mBar, or even at −600 to −800 mBar. In certain embodiments, the vacuum may also be higher than −800 mBar. Independent of the vacuum applied, the API may be dispensed at an ejection pressure of 100 to 1500 mBar, preferably from 200 to 1500 mBar, more preferably from 300 to 1500 mBar, such as 400 to 1500 mBar, in particular 500 to 1500 mBar, more preferably 600 to 1500 mBar, such as 700 to 1500 mBar, even more preferably 800 to 1500 mBar, in particular 900 to 1500 mBar, or even 1000 to 1500 mBar. In certain embodiments, it may even be advantageous to dispense the API at an ejection pressure of more than 1500 mBar.

In case the vacuum assisted metering and filling device is a rotatable drum, said rotatable drum may be assisted by some specific additional features that widen the range of powder characteristics that can be filled. These include fluidization of the powder in the trough near the drum cavities using an ultrasonic transducer (sonicator), which fluidizes the powder adjacent to the probe and allows the API to flow more freely into the drum cavities to overcome poor flow characteristics of some powders. For example, the vacuum assisted metering and filling device may be equipped with a stirrer, and wherein the stirrer is set to 1-4 rotations per cycle, e.g. to from about 2 to about 4 rotations per cycle or from about 1 to about 3 rotations per cycle, or from about 2 to about 3 rotations per cycle. In the alternative, the vacuum assisted metering and filling device may be equipped with an sonic/ultrasonic device, in particular a pogo or pole which pushes and breaks micro-bridging of the powder into the rotatable drum cavities. For example, the pogo or pole applies a frequency of 10,000 Hz to 180,000 Hz, preferably 11,000 Hz to 170,000 Hz, more preferably 12,000 Hz to 160,000 Hz, more preferably 13,000 Hz to 150,000 Hz, more preferably 14,000 Hz to 140,000 Hz, more preferably 15,000 Hz to 130,000 Hz, more preferably 16,000 Hz to 120,000 Hz, more preferably 17,000 Hz to 110,000 Hz, more preferably 18,000 Hz to 100,000 Hz, more preferably 19,000 Hz to 90,000 Hz, more preferably 20,000 Hz to 80,000 Hz, more preferably 21,000 Hz to 70,000 Hz, more preferably 21,500 Hz to 60,000 Hz, more preferably 22,000 Hz to 50,000 Hz, more preferably 22,000 Hz to 40,000 Hz, more preferably 22,000 Hz to 30,000 Hz, and most preferably a frequency of about 22,000 Hz.

The skilled person may choose between a stirrer or the sonic/ultrasonic device depending on the powder rheology of the API. Specifically, if the MPS-15 is 28 or less and/or the WFA is 31° or less, the API is suitable for use in combination with a vacuum assisted metering and filling device equipped with a sonic/ultrasonic device so to assist metering and dispensing of the API. On the other hand, if the SI is more than 1.1, the API is not suitable for use in combination with a vacuum assisted metering and filling device equipped with a stirrer so to assist metering and dispensing of the API. See also the examples herein below.

Other embodiments involve the use of an acoustic device and enclosure which levels the API in the trough and assures a uniform powder bed. A similar acoustic system is also used to condition the powder in the hopper and assure flow from the hopper to the trough. Accordingly, in further embodiments, the vacuum assisted metering and filling device may comprise a powder trough equipped with a fluidization device. An example of such a device is an acoustic speaker, which may or may not be supported by an ultrasonic transducer. In particular embodiments are contemplated wherein feeding occurs from a vibratory hopper to a powder trough, wherein the hopper is preferably activated by a sensor. In preferred embodiments, the sensor is a capacitive sensor. In certain embodiments, feeding occurs from an hopper to a powder trough each equipped with a sonic device using frequencies of 100 to 1000 Hz, wherein the hopper is preferably activated by a sensor, in particular a capacitive sensor, into the powder trough. One may also use frequencies of 200 to 900 Hz, 300 to 800 Hz, 400 to 700 Hz, or 500 to 600 Hz.

The dosage of the API in step (b) may suitably be chosen in the range of 0.1 mg to 550 mg, preferably 0.2 mg to 500 mg, and most preferably 0.25 mg to 450 mg. Preferably, the dosing of the API in step (b) has a relative standard deviation (RSD) of less than 5%, preferably less than 4%, more preferably less than 3%. Usually, the dosing of the API in step (b) is weight-checked using a fill mass measurement technology. For example, the dosing of the API can be weight-checked off-line using brutto-tara weighing. However, in a preferred embodiment, the dosing of the API is weight-checked in real time using a capacitance and/or microwave sensor, in particular by using a capacitance sensor, which allows achievement of 100% fill weigh control. This kind of in-line fill mass verification is available from low throughput to high throughput equipment. The sensor works on the principle of a microwave and/or capacitive, non-contact measurement of the powder falling through a cavity between two capacitor plates. During the measurement the change to the electric field is captured and correlated to the fill weight of the powder.

Nowadays capacitance based sensors are integrated into capsule filler machines and generally used for the dosing of several milligrams of powder. The manner to theoretically set a sensor for sub-milligram range is also common knowledge: the distance of capacitors into the sensor needs to be decreased resulting in a higher electrical field. However, this end up in a smaller diameter of the sensor channels where a powder puck is falling through and measured. For non-optimized powders, this often results in powder pucks collision to the channel walls or even falling on the top edge of sensor or outside the capsule body. Furthermore, dispensing of common powders often results in the formation of tumbling pucks where the consequence is an insufficient sensor reading during dynamic measurement of such falling entities.

For the usage of such capacitance based sensors in the sub-milligram region, a formulation needs to produce a stable powder puck or a unique airborne mass capable to pass through a thin diameter of a sensor channel without breaking into parts or tumbling, as was pursued and obtained by the method of the present invention.

Figure 1:
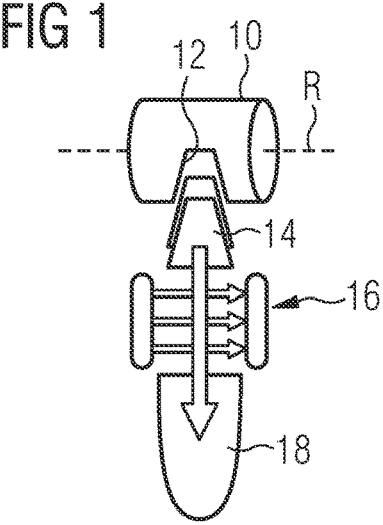
FIG. 1 shows a simplified scheme of a measurement using a capacitance based sensor in a capsule filling machine.

In FIG. 1 a simplified scheme of the measurement using such a sensor in a capsule filling machine is shown. The capsule filling machine comprises a vacuum drum 10 which is rotatable about an axis R and which is provided with a cavity 12. At least a bottom of the cavity 12 is made of a pressure permeable material such as, for example, a filter material which allows the built-up of a desired pressure within the cavity 12. In order to fill the cavity 12 with powder, the vacuum drum 10 is rotated so as to place the cavity 12 below a powder storage (not shown). Furthermore, a pressure below atmospheric pressure is established within the cavity 12. As a result, powder from the powder storage is supplied into the cavity 12, wherein the dosing of the powder can be controlled with a high precision. Thereafter, the vacuum drum 10 is rotated into the position shown in FIG. 1 and a pressure above atmospheric pressure is established within the cavity 12. As a result, a powder puck 14 which is formed in the cavity 12 is ejected from the cavity 12. The powder puck 14 which is formed in the cavity 12 falls through a capacitance based sensor 16 into a capsule body 18 allowing for an in-line measurement of the powder fill weight.

The measurement on-the-fly is almost instantaneous; it is insensitive to machine operational vibrations and especially it determines directly the net fill weight in real time. In addition, these measurement principles are independent from weights variability of capsule shells. These sensors are typically used for monitoring, preferably for 100% sorting of conventional carriers like capsules or into specialized carriers which have the aspect of a tablet, most preferably for real-time release testing. These sensors are typically used for determining the fill weight of a carrier. Procedures have been developed to analytically validate these sensors. These validation procedures have been adapted from Near Infrared Spectroscopy methods used for tablets, where parallel one-to-one testing NIR versus HPLC using Root Mean Square Errors of Predictions is the common practice. As a consequence, when using real-time weight-control using a capacitance and/or microwave sensor, the sensor has a root mean square error of prediction (RSMP) of less than 5%, preferably less than 4.5%, more preferably less than 4%, and most preferably less than 3.5% with respect to an analytical reference tool such as HPLC or balance.

The neat or modified API is then encapsulated into conventional pharmaceutical carriers having at least two parts, such as a lid and a bottom part. In embodiments, the API is consolidated in the bottom part of the pharmaceutical carrier by vibration, shaking or tapping prior to step (c).

Carrier components, bodies and lids, are separately loaded into the machine which is capable to handle, orient and transport the pieces through two independent channels until the powder filling station. After filling, the bottom and the top parts are engaged and pressed together to form the final carrier unit.

The scale up of the technologies can be easily achieved by parallelization of the dosing lines, which allows representative and transferable results through all stages of filling trials in the development process. The sensors system used among the equipment is always the same. This overall combination results in a very flexible filling system, which allows to quickly react on the different clinical and market demands, accommodating a wide range of drug products based on different APIs, using a small footprint on the manufacturing areas and potentially reducing costs of drug development and processing. Accordingly, the present disclosure envisages the use of the above-described method in a continuous process, and/or in a high-throughput process for producing a pharmaceutical product. In this context, high-throughput means at least 25,000 units/h, preferably more than 30,000 units/h, more preferably more than 40,000 units/h, more preferably more than 50,000 units/h, more preferably more than 60,000 units/h, and most preferably at least 70,000 units/h.

Figure 3:
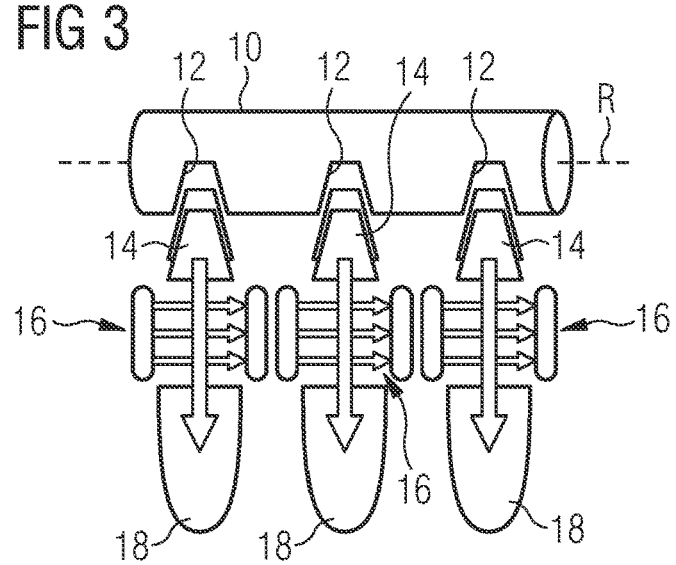
FIG. 3 shows a simplified scheme of a measurement using multiple capacitance based sensors in a capsule filling machine.

In FIG. 3 a simplified scheme of the measurement using multiple sensors 16 in a capsule filling machine is shown (e.g. three tracks). The powder pucks 14 which are generated in a drum 10 with several cavities 12 as described in detail with reference to FIG. 1 above, fall through the sensors 16 into the capsules 18 allowing for an in-line measurement of the powder mass for a multitude of dosing stations, giving individual fill weight values.

Pharmaceutical Carriers

Figure 4:
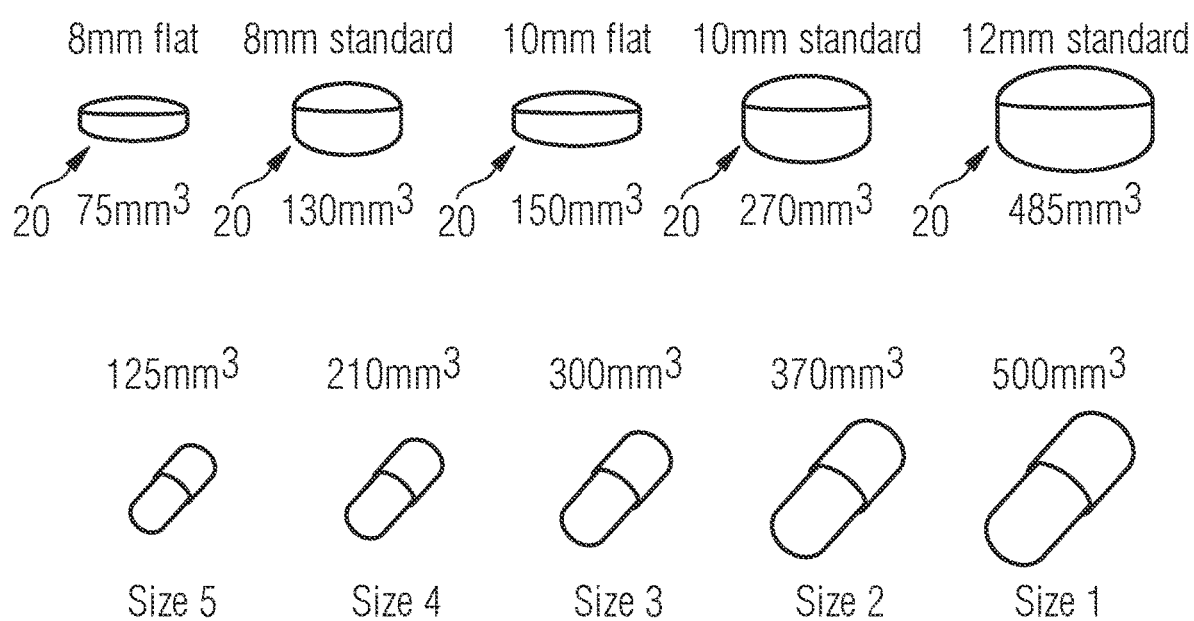
FIG. 4 shows various designs of a pharmaceutical carrier.

Pharmaceutical carriers include oral dosage forms as well as dry powder inhaler mono-dose forms. Pharmaceutical carriers include conventional capsules, such as two-piece capsules made of materials such as gelatin or hypromellose. As an alternative to filling neat or modified API into conventional capsules, the API can also be filled into injection-molded containers, such as the Prescido™ containers described herein. Prescido™ containers are capsules that are filled in the same manner as a capsule, but have the appearance of a film-coated tablet. This creates additional presentation options for marketing to choose from in case a dosage form presentation other than a conventional capsule is desired. FIG. 4 (top row) shows a range of designs of the Prescido™ platform.

As is apparent from FIG. 4, the Prescido™ containers may have different designs and different filling volumes. Specifically, the containers may have various diameters and heights so that an appropriate container may be chosen, for example in dependence on the volume of powder to be filled into the containers. The containers are typically selected to have a tablet shape, such as a disc shape, as opposed to a capsule shape. When considering the lid and bottom and part of the pharmaceutical carrier, a capsule shape would be elongated along a central axis running from a center of the bottom part to a center of the lid part. Thus for a traditional capsule, a ratio of a lateral extension, in particular a diameter of the lid and bottom part to a height of the assembled lid and bottom parts along the central axis would be less than 1:1, such as 0.5:1 or less. For example a type 000 capsule has a diameter of 5.32 mm and a height of 14.3 mm (ratio of 0.37:1) and a type 4 capsule has a diameter of 9.55 mm and a height of 26.1 mm (also a ratio of 0.37:1). By contrast a tablet-shaped carrier has a flatter shape and would have a ratio of greater than 1 (1:1 being essentially a sphere). Thus, the pharmaceutical carrier preferably is designed such that the ratio of a lateral extension, in particular a diameter of the lid and bottom part to the height of the assembled lid and bottom parts is >1, preferably ≥1.4, more preferably ≥1.5, even more preferably ≥2, most preferably ≥2.4 and in particular ≥2.5.

Preferably, the lid part and the bottom part of said pharmaceutical carrier have a complementary closing mechanism. It is further preferred that the complementary closing mechanism is an interlocking snap mechanism. This handling principle is unique and realized for the first time worldwide on a pharmaceutical powder filling machine.

Commercially available capsules are manufactured via a dip coating process. This involves having a reservoir of polymer/water mix and dipping in pins such that they become coated with the mix. The pins are then lifted out of the mix, and the polymer mix on the pin is dried to form a hard capsule before being removed. Prescido™ carriers on the other hand, are manufactured via injection molding. Injection molding involves melting of materials in a screw which is then used to inject the melt at high pressure into a mold where it is rapidly cooled before being ejected. This process has a number of advantages over dip coating: the process can be extremely precise, as electric drivers precisely control movement of the machine, which together with very tight control of process parameters such as temperature, pressure and mold precision, results in high uniformity of parts.

In addition, the use of injection molding opens up opportunities for complicated part geometries. In dip molding, both the outer and inner geometries of the capsule are limited to the shape of the pins whereas the shape of injection molded parts is defined by the mold shape, which can allow multiple features on each face of the carrier.

The composition of traditional capsules is limited to polymers which have correct rheological and film forming properties when dispersed in water. Injection molding however, is a hot melt process, which necessitates very different material properties.

This presents both an opportunity to move away from traditional capsule materials such as gelatin (animal derived, mechanical properties dependent on environmental conditions) and HPMC (dissolution lag time) and a challenge as the injection molding process is very demanding with respect to required material properties. The materials must be thermally stable during the process, have good melt flow properties—particularly under high shear conditions, be flexible enough when cooled to be ejected from the machine and for this application be mechanically strong to enable pharmaceutical processing and dissolve quickly in water. In addition the material must be suitable for human consumption and be approved for pharmaceutical use.

The present inventors have found that a formulation suitable for injection molding can be based on polyethylene oxide (PEO). Ratios of different molecular weight PEO were tested to achieve a formulation with the correct physico-chemical properties.

In this context, the present disclosure further provides a formulation for injection molding of a pharmaceutical carrier, wherein the formulation comprises 43.5-97% (w/w) of one or more polyethylene oxide polymer having a weight average molecular weight of $M_w$ 94,000-188,000; 3-7% (w/w) of an anti-tackifier; and optionally one or more excipients.

Suitable formulations for injection molding of a pharmaceutical carrier have a weight average molecular weight of $M_w$ 94,000-188,000. In preferred embodiments, said polyethylene oxide polymer has a weight average molecular weight of $M_w$ 95,000-185,500, more preferably of $M_w$ 97,500-183,000, more preferably of $M_w$ 100,000-175,000, more preferably of $M_w$ 102,000-165,000, more preferably of $M_w$ 105,000-150,000, even more preferably of 107,500-130,000, and most preferably of $M_w$ 110,000-115,000.

The polyethylene oxide polymer may comprise, preferably consist of, one or more polyethylene oxide having a weight average molecular weight of about $M_w$ 100,000, polyethylene oxide having a weight average molecular weight of about $M_w$ 200,000, polyethylene oxide having a weight average molecular weight of about $M_w$ 300,000, polyethylene oxide having a weight average molecular weight of about $M_w$ 600,000, and polyethylene oxide having a weight average molecular weight of $M_w$ 8,000. Such polyethylene oxides are commercially available.

In a particular preferred embodiment, said polyethylene oxide polymer comprises 35-80% (w/w) of a first polyethylene oxide having a weight average molecular weight of $M_w$ 100,000; and 4-28.5% (w/w) of a second polyethylene oxide having a weight average molecular weight of $M_w$ 200,000. In further preferred embodiments, the formulation may comprise 41-77.5% (w/w), preferably 42-76% (w/w), more preferably 43-75% (w/w), more preferably 45-74% (w/w), more preferably 50-74% (w/w), and most preferably about 73.5% (w/w) of said first polyethylene oxide. In certain preferred embodiments the formulation comprises 4-27.5% (w/w), preferably 5-25% (w/w), more preferably 6-22% (w/w), more preferably 10-21% (w/w), more preferably 11-20.5% (w/w), and most preferably about 20% (w/w) of said second polyethylene oxide.

In further embodiments, the formulation for injection molding of the pharmaceutical carrier comprises 3.5-6.5%, preferably 4-6% (w/w), even more preferably 4.5-5.5% (ww), and most preferably about 5% of the anti-tackifier. A particularly preferred anti-tackifier is talc.

In one embodiment, the formulation comprises 0-6% (w/w) of one or more colorant and/or opacifier, preferably 0.01-5% (w/w) of one or more colorant and/or opacifier, more preferably 0.25-4% (w/w) of one or more colorant and/or opacifier, more preferably 0.5-3% (w/w) of one or more colorant and/or opacifier, more preferably 0.75-2.5% (w/w) of one or more colorant and/or opacifier, more preferably 1-2% (w/w) of one or more colorant and/or opacifier, more preferably 1-1.5% (w/w) of one or more colorant and/or opacifier, and most preferably about 1% (w/w) of one or more colorant and/or opacifier.

It is further preferred that the formulation comprises 0.01-1% (w/w) of an antioxidant, preferably 0.05-0.8% (w/w) of an antioxidant, more preferably 0.1-0.75 (w/w) of an antioxidant, more preferably 0.2-0.7 (w/w) of an antioxidant, more preferably 0.3-0.6 (w/w) of an antioxidant, more preferably 0.4-0.5 (w/w) of an antioxidant, and most preferably about 0.5% (w/w) of an antioxidant.

In certain embodiments, the formulation comprises 30-38% (w/w) of a filler, preferably 32-38% (w/w), more preferably 34-36% (w/w); in particular wherein the filler is talc.

At least one of the lid part and the bottom part has a first wall section with a thickness of 180-250 μm, preferably 185-225 μm, and even more preferably 190-220 μm, and a second wall section with a thickness of 350-450 μm, preferably 375-425 μm, more preferably 390-410 μm, and most preferably about 400 μm.

The thickness of the first wall section has been optimized at 190 to 220 μm. This is thick enough such that, during manufacturing of the pharmaceutical carrier via injection molding, the material can flow through the thin first wall section, and still reliably fill the thicker walled area of the second wall section while being thin enough to achieve the rapid carrier disintegration required to achieve immediate release dissolution profiles of filled compounds. The second wall section has been optimized to a thickness of 400 μm. Here the balance is between having a greater internal volume available for filling, and having the mechanical strength required for filling and handling (including resistance to opening once filled).

A first wall section of the lid part may define at least a portion of a top portion of the lid part. Preferably, the first wall section of the lid part defines the entire top portion of the lid part such that, upon disintegration of the thin first wall section, a rapid and reliable release of compounds filled into the pharmaceutical carrier via the disintegrating top portion of the lid part is achieved.

A second wall section of the lid part may define at least a portion of a side wall portion of the lid part. For example, the second wall section of the lid part may define a shoulder or corner of the lid part which is arranged adjacent to the top portion of the lid part. Specifically, the second wall section of the lid part may extend from the first wall section, i.e. in particular the top portion of the lid part, along an outer circumference thereof, in the direction of the bottom part. This design provides the lid part with the mechanical stability which is required to handle the lid part and to connect it with the bottom part so as to form the pharmaceutical carrier as desired.

In a preferred embodiment of the pharmaceutical carrier, a first wall section of the bottom part defines at least a portion of a bottom portion of the bottom part. Preferably, the first wall section of the bottom part defines the entire bottom portion of the bottom part such that, upon disintegration of the thin first wall section, a rapid and reliable release of compounds filled into the pharmaceutical carrier via the disintegrating bottom portion of the bottom part is achieved.

A second wall section of the bottom part may define at least a portion of a side wall portion of the bottom part. Specifically, the second wall section of the bottom part may extend from the first wall section, i.e. in particular the bottom portion of the bottom part, along an outer circumference thereof, in the direction of the lid part. Preferably, the height of the second wall section of the bottom part is larger than the height of the second wall section of the lid part. In other words, in a preferred embodiment of the pharmaceutical carrier, the bottom part has a generally hollow cylindrical shape and hence defines a "vessel" which may be filled with the pharmaceutical compound. To the contrary, the lid part, which may be provided with a second wall section which merely defines a shoulder or corner surrounding the top portion of the lid part, may have a generally "flat" shape. The larger wall thickness of the second wall section as compared to the first wall section provides the bottom part with a mechanical strength and stability which allows an unhindered filling of the bottom part with the pharmaceutical compound.

In preferred embodiments, the lid part and the bottom part are connected to each other by a complementary closing mechanism. The complementary closing mechanism provides for a reliable and easy to establish connection between the lid part and the bottom part.

More specifically, the closing mechanism may comprise a first snap part which projects from the second wall section of the bottom part so as to face and to interact with a second snap part which projects from the second wall section of the lid part. Upon closing the pharmaceutical carrier, i.e. upon connecting the lid part to the bottom part, at least one of the first and the second snap part may be elastically deformed. When the lid part and the bottom part have reached their final relative positions, i.e. when the lid part is positioned on top of the bottom part so as to seal the interior of the bottom part as desired, the elastic deformation of the at least one of the first and the second snap part may be released in such a manner that the snap parts intact with each other so as to reliably connect the lid part and the bottom part.

For example, the first snap part may comprise a projection which is adapted to engage with a corresponding projection provided on the second snap part so as to counteract separation of the first snap part and the second snap part and thus separation of the lid part and the bottom part. In particular, the projection of the first snap part may comprise a first abutting surface which faces the bottom part and which is adapted to abut against a second abutting surface which is formed on the second snap part and which faces the lid part when the bottom part and the lid part are connected to each other. The first abutting surface formed on the first snap part may extend at an angle of 90 to 150° relative to the side wall portion of the bottom part. The second abutting surface formed on the second snap part may extend at an angle of 90 to 150° relative to the side wall portion of the lid part.

The projection provided on the first snap part may taper in a direction of a free end of the first snap part so as to form a first inclined engagement surface. The first inclined engagement surface may be adapted to engage with a second inclined engagement surface formed on the projection provided on the second snap part which tapers in a direction of a free end of the second snap part. Upon connecting the lid part to the bottom part of the pharmaceutical carrier, the second inclined engagement surface may slide along the first inclined engagement surface thus guiding the projection provided on the first snap part into engagement with the corresponding projection provided on the second snap part. As a result, connecting the lid part to the bottom part is simplified.

One of the first and the second snap part may project from the second wall section of the lid part or the bottom part in the region of an inner circumference of the second wall section, wherein the other one of the first and the second snap part may project from the second wall section of the lid part or the bottom part in the region of an outer circumference of the second wall section of the bottom part. Preferably, the first snap part provided on the bottom part of the pharmaceutical carrier extends from the second wall section of the bottom part in the region of an inner circumference of the second wall section. A thus designed first snap part is particularly suitable for interaction with a second snap part which projects from a particularly shoulder- or corner-shaped second wall section of the lid part in the region of an outer circumference of the second wall section of the lid part.

The closing mechanism may further comprise an inner rib which projects from the second wall section of the lid part or the bottom part in the region of an inner circumference of the second wall section at a distance from the first or the second snap part which projects from the second wall section of the lid part or the bottom part in the region of an outer circumference of the second wall section. In particular, the closing mechanism may comprise inner rib which projects from the second wall section of the lid part in the region of an inner circumference thereof and hence at a distance from the second snap part which projects from the particularly shoulder- or corner-shaped second wall section of the lid part in the region of an outer circumference thereof. As a result, the inner rib and the second snap part define a gap therebetween which is adapted to accommodate the first snap part when the lid part and the bottom part of the pharmaceutical carrier are connected to each other. In the connected state of the lid part and the bottom part, the first snap part is held in place in the gap between the inner rib and the second snap part due to the interaction with the second snap part, i.e. in particular you to the interaction of the first abutting surface formed on the first snap part with the second abutting surface formed on the second snap part, while the inner rib provides for additional mechanical stability and stiffness of the closing mechanism.

It is, however, also conceivable to provide the bottom part of the pharmaceutical carrier with an inner rib, in particular in case the bottom part is provided with a first snap part which projects from the second wall section of the bottom part in the region of an outer circumference thereof and which is adapted to interact with a second snap part which projects from the second wall section of the lid part in the region of an inner circumference thereof. In this case, the inner rib and the first snap part may define a gap therebetween which is adapted to accommodate the second snap part when the lid part and the bottom part of the pharmaceutical carrier are connected to each other.

Preferably, the inner rib is shorter than the snap part arranged opposite to the inner rib. In other words, preferably, the snap part which, together with the inner rib, defines a gap for accommodating the other snap part projects further from the second wall section of the lid part or the bottom part than the inner rib. Further, the inner rib may taper in a direction of a free end of the inner rib so as to form a third inclined engagement surface facing the first or the second snap part which projects from the second wall section of the lid part or the bottom part in the region of an outer circumference of the second wall section and hence is arranged opposite to the inner rib. Preferably, the third inclined engagement surface provided on the inner rib extends substantially parallel to the abutting surface provided on the projection of the snap part arranged opposite to the inner rib. As a result, the snap part which is adapted to be accommodated in the gap defined between the inner rib and the snap part arranged opposite to the inner rib upon connecting the lid part and the bottom part of the pharmaceutical carrier is guided into engagement with the snap part arranged opposite to the inner rib. Additionally, the inner rib stabilizes the snap closure against opening.

In a preferred embodiment of the pharmaceutical carrier, the first wall section of the lid part, in particular in a region which is defined by a material injection point into a mold upon manufacturing of the lid part, is provided with a depression. This depression may have a wall thickness that is larger than the wall thickness of the remaining part of the first wall section, but smaller than the wall thickness of the second wall section of the lid part. For example, the depression may be arranged in a central region of a top portion of the lid part. A sign which indicates a cavity in which the lid part was molded on a multicavity molding tool during an injection molding process may be imprinted onto a surface, in particular an inner surface of the depression. This allows for automatic sorting of the lid parts by cavity for applications where tight weight uniformity is required.

Alternatively or additionally thereto, the first wall section of the bottom part, in particular in a region which is defined by a material injection point into a mold upon manufacturing of the bottom part, is provided with a depression. This depression may have a wall thickness that is larger than the wall thickness of the remaining part of the first wall section, but smaller than the wall thickness of the second wall section of the lid part. For example, the depression may be arranged in a central region of a bottom portion of the bottom part. A sign which indicates a cavity in which the bottom part was molded on a multicavity molding tool during an injection molding process may be imprinted onto a surface, in particular an inner surface of the depression. This allows for automatic sorting of the bottom parts by cavity for applications where tight weight uniformity is required.

At least one of the lid part and the bottom part, in the region of an inner surface thereof, may be provided with a plurality of inner protrusions which project radially inwards from an inner surface of the second wall section and/or an inner surface of the inner rib. In case the lid part or the bottom part which is provided with inner protrusions also is provided with an inner rib, the inner protrusions, in a direction of a central axis of the lid part or the bottom part, may extend from the top portion of the lid part or the bottom portion of the bottom part along the second wall section of the lid part of the bottom part and finally along the inner rib which projects from the second wall section in the region of an inner circumference thereof. In case the lid part of the bottom part which is provided with inner protrusions does not comprise an inner rib, the inner protrusions, in a direction of a central axis of the lid part or the bottom part, may extend from the top portion of the lid part or the bottom portion of the bottom part along the second wall section of the lid part or the bottom part. At least one of and in particular each of the inner protrusions may comprise a projecting nose which projects beyond the second wall section and/or the inner rib.

The inner protrusions, in particular when being provided with projecting noses, reduce a phenomenon termed 'nesting', i.e. an adherence of the parts and/or bottom parts stacked on top of each other. As a result, difficulties during manual and automated handling which may be caused by 'nests' of stacked parts which are difficult to separate can be eliminated.

In a preferred embodiment of the pharmaceutical carrier, the bottom part is provided with an angled balcony. The angled balcony may be formed in the region of an outer surface of the second wall section of the bottom part, in particular adjacent to the first snap part. The angled balcony may be inclined radially outwards from an outer circumference of the first snap part towards an outer surface of the second wall section. Powdery compounds to be filled into the pharmaceutical carrier which inadvertently fall onto the balcony of the bottom part upon filling or closing the pharmaceutical carrier can easily be removed.

Figure 5:
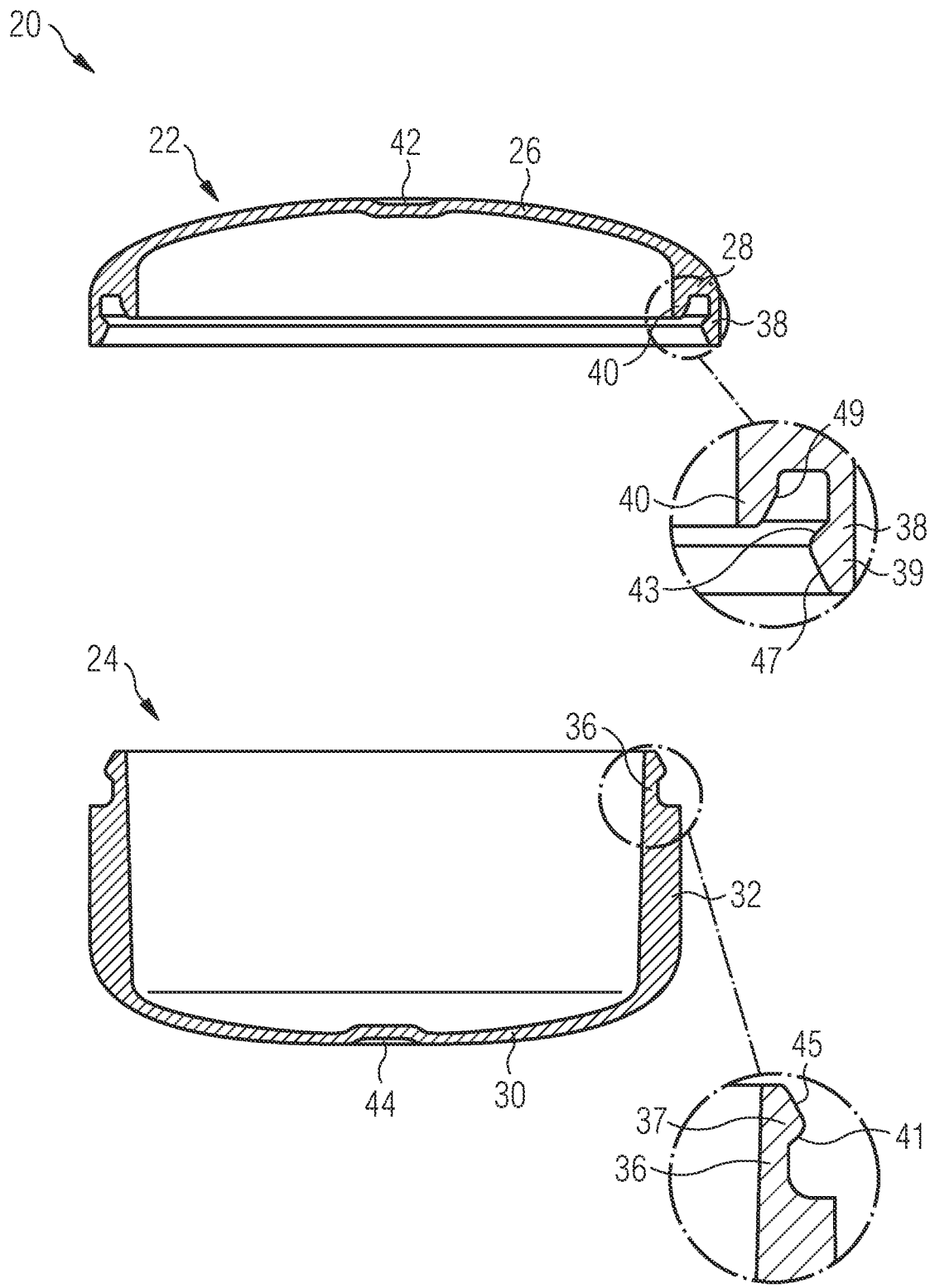
FIG. 5 shows sectional views of a lid part (left) and a bottom part (right) of an exemplary embodiment of the pharmaceutical carrier according to FIG. 4 including detailed views of a closing mechanism provided on the lid part and the bottom part.
Figure 6:
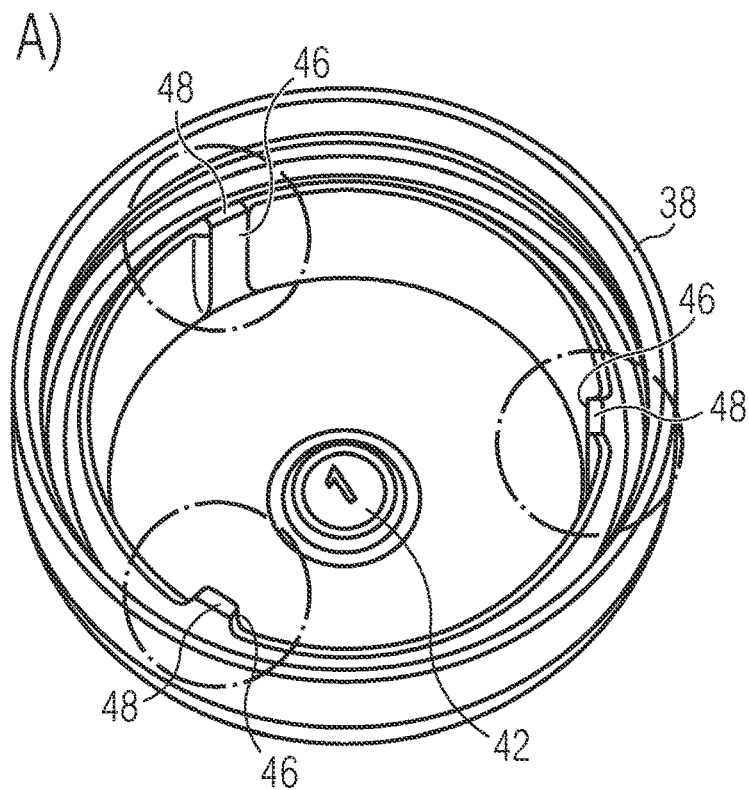
FIG. 6A shows a three-dimensional view of the carrier bottom part as shown on the right in FIG. 5.
FIG. 6B shows a further detailed view of the closing mechanism provided on the lid part and the bottom part of the pharmaceutical carrier according to FIG. 5.
Figure 6:
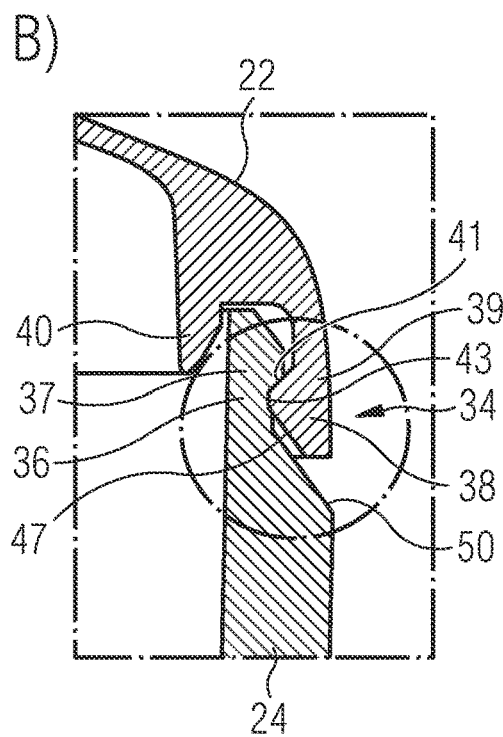

An exemplary pharmaceutical carrier 20 is shown in FIGS. 5, 6A and 6B. The carrier 20 comprises a lid part 22 and a bottom part 24. The lid part 22, which is shown on the left in FIG. 5 and in FIG. 6A, comprises a first wall section 26 which defines a top portion of the lid part 22 and a second wall section 28 which defines a side wall portion of the lid part 22. In particular, the second wall section 28 of the lid part 22 defines a shoulder or corner of the lid part 22 which is arranged adjacent to the top portion of the lid part 22. Specifically, the second wall section 28 of the lid part 22 extends from the top portion of the lid part 22, along an outer circumference thereof, in the direction of the bottom part 24. The first wall section 26 has a wall thickness that is smaller than a wall thickness of the second wall section 28. In the preferred embodiment of the carrier 20 shown in FIG. 5, the first wall section 26 has a wall thickness of 190 to 220 μm, whereas the second wall section 28 has a wall thickness of about 400 μm.

Similarly, the bottom part 24, which is shown on the right in FIG. 5, comprises a first wall section 30 which defines a bottom portion of the bottom part 24 and a second wall section 32 which defines a side wall portion of the bottom part 24. The second wall section 32 of the bottom part 24 extends from the bottom portion of the bottom part 24 along an outer circumference thereof in the direction of the lid part 22. The first wall section 30 has a wall thickness that is smaller than a wall thickness of the second wall section 32. In the preferred embodiment of the carrier 20 shown in FIG. 5, the first wall section 30 has a wall thickness of 190 to 220 μm, whereas the second wall section 32 has a wall thickness of about 400 μm.

The lid part 22 and the bottom part 24 are connected to each other by means of a complementary closing mechanism 34 which is illustrated in greater detail in the detailed views shown in FIG. 5 as well as in FIG. 6B. The closing mechanism 34 comprises a first hook-shaped snap part 36 which projects from the second wall section 32 of the bottom part 24 in the region of an inner circumference of the second wall section 32. The first hook-shaped snap part 36 faces and interacts with a correspondingly shaped second hook-shaped snap part 38 which projects from the second wall section 28 of the lid part 22 in the region of an outer circumference of the second wall section 28. It would, however, also be conceivable to provide the closing mechanism 34 with a first snap part 36 which projects from the second wall section 32 of the bottom part 24 in the region of an outer circumference of the second wall section 32 and a second snap part 36 which projects from the second wall section 28 of the lid part 22 in the region of an inner circumference of the second wall section 28.

As becomes apparent from the detailed views shown in FIG. 5 and FIG. 6B, the first snap part 36 comprises a projection 37 which, upon connecting the lid part 22 and the bottom part 24, is adapted to engage with a corresponding projection 39 provided on the second snap part 38. The projection 37 of the first snap part 36 comprises a first abutting surface 41 which faces the bottom part 24. Similarly, the projection 39 of the lid part 22 comprises a second abutting surface 43 which faces the lid part 22. The first abutting surface 41 formed on the projection 37 of the first snap part 36 extends at an angle of approximately 135° relative to the side wall portion of the bottom part 24. The second abutting surface 43 formed on the projection 39 of the second snap part 38 extends at an angle of approximately 135° relative to the side wall portion of the lid part 22. Further, the projection 37 provided on the first snap part 36 tapers in a direction of a free end of the first snap part 36 so as to form a first inclined engagement surface 45. Similarly, the projection 39 provided on the second snap part 38 also tapers in a direction of a free end of the first snap part 38 so as to form a second inclined engagement surface 47.

The closing mechanism 34 further comprises an inner rib 40 which projects from the shoulder- or corner-shaped second wall section 28 of the lid part 22 in the region of an inner circumference of the second wall section 28. Hence, the inner rib 40 projects from the second wall section 28 of the lid part 22 at a distance from the second snap part 36 which projects from the second wall section 28 of the lid part 22 in the region of an outer circumference of the second wall section 28. As a result, the inner rib 40 and the second snap part 38 define a gap therebetween which is adapted to accommodate the first snap part 36 when the lid part 22 and the bottom part 24 of the pharmaceutical carrier 20 are connected to each other. However, in case the lid part 22 is provided with a second snap part 38 which is arranged in the region of an inner circumference of the second wall section 28 so as to interact with a first snap part 38 which is arranged in the region of outer circumference of the second wall section 32 of the bottom part 24, it is also conceivable that the closing mechanism 34 comprises an inner rib 40 which projects from the second wall section 32 of the bottom part 24 in the region of an inner circumference of the second wall section 32. In this case it is the first snap part 36 which, together with the inner rib 40, defines a gap which is adapted to accommodate the second snap part 38 when the lid part 22 and the bottom part 24 of the pharmaceutical carrier 20 are connected to each other.

The inner rib 40 is shorter than the second snap part 38 arranged opposite to the inner rib 40, i.e. the second snap part 38 projects further from the second wall section 28 of the lid part 22 than the inner rib 40. Further, the inner rib 40 tapers in a direction of a free end of the inner rib 40 so as to form a third inclined engagement surface 49 facing the second snap part 38 which projects from the second wall section 28 of the lid part 22 in the region of an outer circumference of the second wall section 28 and opposite to the inner rib 40. The third inclined engagement surface 49 extends substantially parallel to the second abutting surface 43 provided on the projection 39 of the second snap part 38 arranged opposite to the inner rib 40. In case the lid part 22 is provided with a second snap part 38 which is arranged in the region of an inner circumference of the second wall section 28 so as to interact with a first snap part 38 which is arranged in the region of outer circumference of the second wall section 32 of the bottom part 24, the third inclined engagement surface 49 formed on the inner rib 40 may face the first snap part 36 which projects from the second wall section 32 of the bottom part 24 in the region of an outer circumference of the second wall section 32 and opposite to the inner rib 40

Upon closing the pharmaceutical carrier 20, i.e. upon connecting the lid part 22 to the bottom part 24, the first inclined engagement surface 45 provided on the projection 37 of the first snap part 36 comes into contact with the second inclined engagement surface 47 provided on the projection 39 of the second snap part 38. When the lid part 22 approaches the bottom part 24, the second inclined engagement surface 47 slides along the first inclined engagement surface 45 which results in a slight elastic deformation of the first and the second snap part 36, 38. Specifically, the first snap part 38 is slightly bent radially inwards, whereas the second snap part 36 is slightly bent radially outwards. Inward bending of the first snap part 38 is, however, limited by the inner rib 40. Further, the third inclined engagement surface 49 provided on the inner rib 40 guides the second snap part 38 into its final position in the gap defined between the second snap part 38 and the inner rib 40, see FIG. 6B.

When the lid part 22 and the bottom part 24 have reached their final relative positions, i.e. when the lid part 22 is positioned on top of the bottom part 24 so as to seal the interior of the bottom part 24, the elastic deformation of the first and the second snap part 36, 38 is released and the first abutting surface 41 provided on the projection 37 of the first snap part 36 abuts against the second abutting surface 43 provided on the projection 39 of the second snap part 38. The interaction between the first and the second abutting surface 41, 43 contacts separation of the bottom part 24 and the lid part 22. The inner rib 40 provides for additional mechanical stability and stiffness of the closing mechanism 34.

The first wall section 26 of the lid part 22, in a central region which is defined by a material injection point into a mold upon manufacturing of the lid part 22, is provided with a depression 42 which has a wall thickness that is larger than the wall thickness of the remaining part of the first wall section 26, but still smaller than the wall thickness of the second wall section 28 of the lid part 22. A number, in the drawings the number "1", is imprinted onto an inner surface of the depression 42 which indicates a cavity in which the lid part 22 was molded on a multicavity molding tool. Similarly, also the first wall section 30 of the bottom part 24, in a central region which is defined by a material injection point into a mold upon manufacturing of the bottom part 24, is provided with a depression 44 which has a wall thickness that is larger than the wall thickness of the remaining part of the first wall section 30, but still smaller than the wall thickness of the second wall section 32 of the bottom part 24. A number (not shown in the drawings) is imprinted onto an inner surface of the depression 44 which indicates a cavity in which the bottom part 24 was molded on a multicavity molding tool.

As becomes apparent from FIG. 6A, the lid part 22 further is provided with a plurality of inner protrusions 46 which project radially inwards from an inner surface of the second wall section 28 and an inner surface of the inner ring 40, respectively. In the specific embodiment of a lid part 22 shown in the drawings, three inner protrusions 46 are provided. It is, however, also conceivable to provide the lid part 22 with less than or more than three inner protrusions 46. The inner protrusions 46 serve to prevent jamming of parts 22, which are stacked on top of each other during handling. Each of the inner protrusions 46 comprises a nose 48 which projects from the inner rib 40 and which further reduces the risk of jamming of parts 22 stacked on top of each other. In the embodiment of the carrier 20 which is illustrated in the drawings, only the lid part 22 is provided with inner protrusions 46. It is, however, also conceivable that alternatively or additionally also the bottom part 24 of the carrier 20 is provided with inner protrusions as described herein.

Finally, as becomes apparent from FIG. 6B, the bottom part 24 is provided with an angled balcony 50 which is formed in the region of an outer surface of the second wall section 32 adjacent to the first hook-shaped snap part 36 and which is inclined radially outwards from an outer circumference of the hook-shaped snap part 38 towards an outer surface of second wall section 32. Powder which inadvertently falls onto the balcony 50 upon closing the carrier 20 can easily be removed.

Advantageously, the pharmaceutical carrier exhibits a standard mass deviation of the respective carrier parts of less than 1 mg, preferably less than 0.8 mg, more preferably less than 0.6 mg, even more preferably less than 0.4 mg, still more preferably less than 0.3 mg, still even more preferably less than 0.2 mg, and most preferably less than 0.1 mg.

The invention is further described by the following embodiments.

1. A method of preparing a pharmaceutical product, comprising the steps of
   (a) providing an active pharmaceutical ingredient (API) which complies with at least five of the following parameters (i)-(viii) as determined by using a FT4 powder rheometer:
      (i) specific basic flow energy (sBFE) of at most 60 mJ/g;
      (ii) stability index (SI) of 0.75 to 1.25,
      (iii) specific energy (SE) of at most 10 mJ/g;
      (iv) major principle stress at 15 kPa (MPS-15) of at most 40;
      (v) flow function at 15 kPa (FF-15) of at least 1.3,
      (vi) consolidated bulk density at 15 kPa (CBD-15) of at least 0.26 g/mL;
      (vii) compressibility of at most 47%; and
      (viii) wall friction angle (WFA) of at most 40°;
   (b) dispensing the API of step (a) into a bottom part of a pharmaceutical carrier using a vacuum assisted metering and filling device; and
   (c) encapsulating the bottom part of said pharmaceutical carrier with a complementary lid part of said pharmaceutical carrier, thereby producing a pharmaceutical product.
2. The method of embodiment 1, wherein
   (i) the sBFE is at most 25 mJ/g, in particular at most 6 mJ/g; and/or
   (ii) the SI is 0.83 to 1.18, in particular 0.9 to 1.1; and/or
   (iii) the SE is at most 8 mJ/g, in particular at most 6 mJ/g; and/or
   (iv) the MPS-15 is at most 33, in particular at most 25; and/or
   (v) the FF-15 is at least 3, in particular at least 10; and/or
   (vi) the CBD-15 is at least 0.45 g/mL, in particular at least 0.6 g/mL; and/or
   (vii) the compressibility is at most 35%, in particular 3-15%; and/or
   (viii) the WFA is at most 34°, in particular at most 28°.
3. The method of embodiment 1 or 2, wherein parameters (i)-(viii) are determined by using a FT4 powder rheometer and the powder characterization methods per measurement cylinder diameter
   (i) 25 mm_1C_Split_Rep+VFR_R01;
   (ii) 25 mm_Shear_15 kPa;
   (iii) 25 mm_Compressibility_1-15 kPa; and
   (iv) 25 mm_Wall Friction_30 kPa.
4. The method of any one of embodiments 1-3, wherein the vacuum assisted metering and filling device is a rotatable drum (10).
5. The method of embodiment 4, wherein the vacuum is applied into the drum cavity at −100 to −800 mBar; and/or the API is dispensed at an ejection pressure of 100 to 1500 mBar.
6. The method of embodiment 4 or 5, wherein the vacuum assisted metering and filling device is a rotatable drum (10), which is either equipped with a stirrer or with a sonic/ultrasonic device so to assist metering and dispensing of the API.
7. The method of embodiment 6, wherein the vacuum assisted metering and filling device is equipped with a stirrer, and wherein the stirrer is set to 1-4 rotations per cycle.
8. The method of embodiment 6, wherein the vacuum assisted metering and filling device is equipped with a sonic/ultrasonic device, in particular a pogo or pole which pushes and breaks micro-bridging of the powder into the rotatable drum cavities, in particular wherein the pogo or pole applies a frequency of 10000 Hz to 180,000 Hz, preferably about 22,000 Hz.
9. The method of any one of embodiments 6-8, wherein
   (i) if the MPS-15 is 28 or less and/or the WFA is 31 or less, the API is suitable for use in combination with a vacuum assisted metering and filling device equipped with a sonic/ultrasonic device so to assist metering and dispensing of the API; and
   (ii) if the SI is more than 1.1, the API is not suitable for use in combination with a vacuum assisted metering and filling device equipped with a stirrer so to assist metering and dispensing of the API.
10. The method of any one of embodiments 4-8, wherein the vacuum assisted metering and filling device comprises a powder trough equipped with a fluidization device, in particular an acoustic speaker, in addition with an ultrasonic transducer.
11. The method of embodiment 10, wherein feeding occurs from a vibratory hopper to a powder trough, wherein the hopper is preferably activated by a sensor, in particular a capacitive sensor, into the powder trough.
12. The method of embodiment 11, wherein feeding occurs from an hopper to a powder trough each equipped with a sonic device using frequencies of 100 to 1000 Hz, wherein the hopper is preferably activated by a sensor, in particular a capacitive sensor, into the powder trough.
13. The method of any one of embodiments 1-12, wherein the dosing of the API is weight-checked using a fill mass measurement technology.
14. The method of embodiment 13, wherein the dosing of the API is weight-checked in real time using a capacitance and/or microwave sensor (16), in particular by using a capacitance sensor.
15. The method of embodiment 14, wherein the sensor (16) has a root mean square error of prediction (RMSP) of less than 5%, preferably less than 4.5%, more preferably less than 4%, and most preferably less than 3.5% with respect to an analytical reference toolsuch as HPLC or balance.
16. The method of embodiment 13, wherein the dosing of the API is weight-checkededled off-line using brutto-tara weighing.
17. The method of any one of embodiments 1-16, wherein the API comprises at most 5% (w/w) of an additive, preferably at most 4% (w/w), more preferably at most 3% (w/w), even more preferably at most 2% (w/w), and most preferably at most 1% (w/w).

18. The method of embodiment 17, wherein the one or more additive is selected from the group of hydrophobic colloidal silicon dioxide, hydrophilic colloidal silicon dioxide, magnesium stearate, stearic acid, sodium stearyl fumarate, sodium lauryl sulfate, poloxamer 188, hydrogenated vegetable oil, or any combination thereof.

19. The method of any one of embodiments 1-18, wherein step (a) further comprises sieving of the API, wherein sieving is selected from sieving through conical sieving equipment, oscillating sieving, or screen sieving assisted by ultrasonic vibration.

20. The method of any one of embodiments 1-19, wherein the dosage of the API in step (b) is in the range of 0.1 mg to 550 mg, preferably 0.2 mg to 500 mg, and most preferably 0.25 mg to 450 mg.

21. The method of any one of embodiments 1-20, wherein the dosing of the API in step (b) has a relative standard deviation (RSD) of less than 5%, preferably less than 4%, more preferably less than 3%.

22. The method of any one of embodiments 1-21, wherein the API is consolidated in the bottom part of the pharmaceutical carrier by vibration, shaking or tapping prior to step (c).

23. The method of any one of embodiments 1-22, wherein at least one of the lid part (22) and the bottom part (24) of the pharmaceutical carrier (20) has a first wall section (26, 30) with a thickness of 180-250 µm, preferably 185-225 µm, and even more preferably 190-220 µm, and a second wall section (28, 32) with a thickness of 350-450 µm, preferably 375-425 µm, more preferably 390-410 µm, and most preferably about 400 µm.

24. The method of any one of embodiments 1-23, wherein the lid part (22) and the bottom part (24) are connected to each other by a complementary closing mechanism (34); in particular wherein the closing mechanism (34) comprises a first snap part (36) which projects from the second wall section (32) of the bottom part (24) so as to face and to interact with a second snap part (38) which projects from the second wall section (28) of the lid part (22);

more particularly wherein the first snap part (36) comprises a projection (37) adapted to engage with a corresponding projection (39) provided on the second snap part (38) so as to counteract separation of the first snap part (36) and the second snap part (38) and thus separation of the lid part (22) and the bottom part (24);

even more particularly wherein the projection (37) provided on the first snap part (36) tapers in a direction of a free end of the first snap part (36) so as to form a first inclined engagement surface (45) adapted to engage with a second inclined engagement surface (47) formed on the projection (39) provided on the second snap part (38) which tapers in a direction of a free end of the second snap part (36);

most preferably wherein one of the first and the second snap part (36, 38) projects from the second wall section (28, 32) of the lid part (22) or the bottom part (24) in the region of an inner circumference of the second wall section (28, 32), and wherein the other one of the first and the second snap part (36, 38) projects from the second wall section (28, 32) of the lid part (22) or the bottom part (24) in the region of an outer circumference of the second wall section (28, 32).

25. The method of embodiment 24, wherein the closing mechanism (34) further comprises an inner rib (40) which projects from the second wall section (28) of the lid part (22) or the bottom part (24) in the region of an inner circumference of the second wall section (28, 32) at a distance from the first or the second snap part (36, 38) which projects from the second wall section (28, 32) of the lid part (22) or the bottom part (24) in the region of an outer circumference of the second wall section (28, 32);

in particular wherein the inner rib (40) tapers in a direction of a free end of the inner rib (40) so as to form a third inclined engagement surface (49) facing the first or the second snap part (36, 38) which projects from the second wall section (28, 32) of the lid part (22) or the bottom part (24) in the region of an outer circumference of the second wall section (28, 32).

26. The method of any one of embodiments 1-25, wherein the bottom part (24) is provided with an angled balcony (50) which is formed in the region of an outer surface of the second wall section (32) of the bottom part (24), in particular adjacent to the first snap part (36), and which is inclined radially outwards, in particular from an outer circumference of the first snap part (36) towards an outer surface of second wall section (32).

27. Use of the method of any one of embodiments 1-26 in a continuous process.

28. Use of the method of any one of embodiments 1-26 in a high-throughput process for producing a pharmaceutical product.

In the following, the present invention as defined in the embodiments is further illustrated by the following examples, which are not intended to limit the scope of the present invention. All references cited herein are explicitly incorporated by reference.

EXAMPLES

A standard FT4 powder rheometer offers at least 6 powder characterization methods (per measurement cylinder diameter). Those selected for analysis are 25 mm_1C_Split_Rep+VFR_R01;
25 mm_Shear_15 kPa;
25 mm_Compressibility_1-15 kPa;
25 mm_Wall Friction_30 kPa.

Each characterization method produces several kind of response parameters (default or manually selectable). A set of complete powder characterizations (at least 22 response parameters per row) were measured for more than 350 different powders and more than 60 different compounds using a standard FT4 powder rheometer and compiled in a database. The various parameters were correlated to the respective filling behavior in order to determine a set of parameters and parameter ranges which is capable of distinguishing and predicting filling behavior of powders. The following 8-parameter model was obtained:

| Range\variable | sBFE | SI | SE | MPS-15 | FF-15 | CBD-15 | CPS | WFA |
|---|---|---|---|---|---|---|---|---|
| At most | <60 | 0.75-1.25 | <10 | <40 | >1.3 | >0.26 | <47% | <40° |
| More preferably at most | <25 | 0.83-1.18 | <8 | <33 | >3 | >0.45 | <35% | <34° |
| most preferably at most | <6 | 0.9-1.1 | <6 | <25 | >10 | >0.6 | 3-15% | <28° | wherein the parameters are:
sBFE: Specific Basic Flow Energy (mJ/g): obtained from BFE (obtained from standard FT4 test platform) divided by the split mass of the sample.
SI: Stability Index, standard variable, dimensionless.
SE: Specific Energy (mJ/g), standard variable
MPS @ 15 kPa: major Principal Stress, standard variable
FF @ 15 kPa: Flow function (dimensionless), from shear cell, standard variable
CBD @ 15 kPa: Consolidated Bulk Density (g/mL), standard variable (from shear cell)
CPS: Compressibility (%), standard variable
WFA: Wall Friction Angle (degree°), standard variable.

If four of the parameters are outside the indicated ranges, the powder is predicted as borderline in term of manufacturability. If more than four of the parameters are outside the indicated ranges, the powder is most probably and practically unworkable in any automatic machine here described as neat API. Moreover, it was found that if the MPS is very high, and in minor manner also the WFA is high, the powder is prone to build up in the filling and dosing device. This is a negative characteristic for sonic/ultrasonic filling technology. On the other hand, if the SI is too high, the powder changes its characteristics over time, rendering it more sensitive to shear force. Such a powder is less workable in the standard vacuum drum filling technology which uses a stirrer.

The found '8-parameter model' is capable of distinguishing and predicting filling behavior of powders among the database, where also the experimental response/scoring on a capsule filler equipment is reported for at least 40% of the powders. The following cases demonstrate the capability of the 8-parameter model to predict and drive the development of powders suitable for dosing as neat API. Numbers in bold fall outside of the desired range.

The majority of these powders are discussed in the following examples.

Example 1

A large production of Pharmaceutical drug product containing LEE011 was required since early stage in the development life cycle of such compound. Several batches of API were crystallized, sieved and filled into capsule through the here described equipment platform platform using both types of vacuum drum equipment, Standard and Sonic fillers. Filling performance was sufficiently good for the majority of used powder variants especially in term of dose uniformity (dose range from 10 to 250 mg), however powder behaviour/flowability in the machine hopper and friction generation among parts in movements were, on average, challenging aspects causing some issues and process downtimes during very long runs. Whereas standard filling technology, especially after some optimizations, could cope with such intrinsic difficulties associated with LEE011 powders (some millions of capsule units successfully filled), the Sonic filling technology has shown important episodes of process downtime and damage to components due to powder build up inside the powder trough, especially when the MPS parameter was measured as particularly high. The '8-parameter model' was capable to advice against the selection of Sonic filling for powders having concurrently high MPS and WF, even though one example (6.) was able to be filled despite these values.

Example 2

Filling neat drug substance at a certain throughput, which is suitable for the manufacturing of large batches, is not commonly established in industry. For the API LXS196,

| Variable/example Group | sBFE | SI 1 | SE | MPS-15 | FF-15 2 | CBD-15 | CPS 3 | WFA 4 | Standard Vacuum drum filler | Sonic filler Vacuum drum |
|---|---|---|---|---|---|---|---|---|---|---|
| 1. LEE011 | 38 | 0.9 | 8.2 | 42 | 5.8 | 0.6 | 26 | 40 | + | − |
| 2. NBU928 | 5 | 1.4 | 6.6 | 28 | 2.5 | 0.5 | 39 | 31 | − | + |
| 3. FTY720 +0.9% Aerosil | 3 | 1.0 | 6.7 | 6 | 1.4 | 0.2 | 26 | 18 | + | + |
| 4. Lactose 125M (ideal powder) | 16 | 1.0 | 5 | 25 | 51 | 0.8 | 13 | 27 | | |
| 5. LX5196 | 26 | 1.1 | 6.3 | 27 | 15 | 0.7 | 11 | 29 | | |
| 6. CDZ173 | 29 | 1.5 | 19 | 50 | 1.4 | 0.26 | 43 | 50 | − | + |
| 7. CDZ173 | 82 | 1.1 | 10.1 | 9.6 | 5 | 0.2 | 56 | 37 | − | − | particle properties and filling process were developed in an integrated way. The described method enabled to manufacture LXS196 capsules for clinical supply at a throughput superior than 40'000 capsules within 6 hours. The percentage of good capsules was 98.8% of the total number of produced capsules. A simplified manufacturing process was realized, only performing sieving and encapsulation (incl. 100% weight control by capacitance sensor, dedusting and metal checking) of the neat drug substance. As well, doses of up to 400 mg were filled into capsule size 0. Furthermore, applying an in-house developed high dose technology (tapping mechanism), doses of above 450 mg were encapsulated on automated drum filler equipment.

Example 3

Dosing powder containing sub-milligram amounts of API is at the cutting edge of capsule filling. To overcome challenges, in galenical development the standard process for low dose formulation describes the API being blended and diluted with excipients within serval blending steps, which allows the final dosing of some milligrams of the diluted blend into capsules. The same is true for machine equipped with capacitance sensors for mass checking which are typically used for capsule filling starting from a minimum of some milligrams and above.

The herein described method allows to process neat API of FTY720, which contains less than 1% of additive (>99% of API), with optimal physical properties, suitable for a precise capsule filling at very low dose such as 0.5 and 0.25 mg, using a process analytical technology for 100% fill mass confirmation which corresponds to 100% content uniformity check, for the first time pushed at a sub-milligram range. Moreover the method of the present disclosure presents a very simple process in comparison with current marketed formulation, where several process steps are used (i.e. several sieving-blending passages to dilute the blend step by step).

The final pharmaceutical product showed also a longer shelf life than corresponding marketed formulation as only two components are in direct contact with the drug substance (Silicon dioxide and Gelatin).

Example 4

NBU928 is a fumarate salt with a challenging crystallization process. The resulting particles typically have an elongated aspect ratio, crystals are lath shaped up to 400 μm long with strong agglomeration tendency. Such kind of crystal shape give a resulting powder bulk which is not directly processable in any capsule filler equipment. Therefore the API powder was subjected to a Particle Engineering treatment to selectively grow the shot side of the crystal then it was milled down through a pin mill equipment obtaining a quite regular fragmentation, leading to smaller particles with more steady aspect ratio, free of agglomeration, with an average diameter (X50) of about 25 μm. Rheological characteristics of the new milled API powder (lot #NBU928-metzgch4-001-03) suggest a difficult processability with standard PDP filling technology (powder bridging in the hopper under the action of stirrer shear force, due to a certain instability of the bulk aeration level is expected) but a perfect processability in the Sonic Filler vacuum drum equipment. In fact, very good capsule filling performance was obtained in the required dose range of 5 to 50 mg.

Example 5

CDZ173 is a mono-phosphate salt compound. It is characterized by needle shaped crystals with aspect ratio >10, agglomerated/fused rod-like crystals, very low bulk density (always <0.2 g/mL, very often <0.12 g/mL). It is here reported in two different variants (milled and un-milled). Line 6 was borderline fillable (at very low speed/throughput) even though its characteristics fall outside the parameters for our model (4/8 criteria met) while material in line 7 was not fillable with the processing method of the present disclosure, unless an important change in the crystallization is pursued (not described here).

The invention claimed is:
1. A method of preparing a pharmaceutical product, comprising the steps of
   (a) providing a neat active pharmaceutical ingredient (API) which complies with at least five of the following parameters (i)-(viii) as determined by using a FT4 powder rheometer:
      (i) specific basic flow energy (sBFE) of at most 60 mJ/g;
      (ii) stability index (SI) of 0.75 to 1.25;
      (iii) specific energy (SE) of at most 10 mJ/g;
      (iv) major principle stress at 15 kPa (MPS-15) of at most 40;
      (v) flow function at 15 kPa (FF-15) of at least 1.3;
      (vi) consolidated bulk density at 15 kPa (CBD-15) of at least 0.26 g/mL;
      (vii) compressibility of at most 47%; and
      (viii) wall friction angle (WFA) of at most 40°;
   (b) dispensing the neat API of step (a) into a bottom part of a pharmaceutical carrier using a vacuum assisted metering and filling device; and
   (c) encapsulating the bottom part of said pharmaceutical carrier with a complementary lid part of said pharmaceutical carrier, thereby producing a pharmaceutical product.
2. The method of claim 1, wherein at least one of the parameters is selected from parameters (i) to (iii) and at least one of the parameters is selected from parameters (iv) to (vi).
3. The method of claim 2 wherein at least one of the parameters is parameter (i) or (iii) and at least one of the parameters is parameter (iv) or (v).
4. The method of claim 1, wherein at least one of the parameters is parameter (vii) or (viii).
5. The method of claim 1, wherein the pharmaceutical product is an oral dosage form.
6. The method of claim 1, wherein the vacuum assisted metering and filling device is a rotatable drum.
7. The method of claim 6, wherein the vacuum assisted metering and filling device is a rotatable drum, which is either equipped with a stirrer or with a sonic/ultrasonic device to assist metering and dispensing of the API;
   wherein if the vacuum assisted metering and filling device is equipped with a stirrer, the stirrer is set to 1-4 rotations per cycle; and
   wherein if the vacuum assisted metering and filling device is equipped with an ultrasonic device, which is a pogo or pole which pushes and breaks micro-bridging of the powder into the rotatable drum cavities, the pogo or pole applies a frequency of 10,000 Hz to 180,000 Hz.
8. The method of claim 6, wherein the vacuum assisted metering and filling device comprises a powder trough equipped with a fluidization device and an ultrasonic transducer.
9. The method of claim 8, wherein feeding occurs from a vibratory hopper to a powder trough, wherein the hopper is activated by a capacitance sensor, into the powder trough.

10. The method of claim 8, wherein feeding occurs from a hopper to a powder trough each equipped with a sonic device using frequencies of 100 to 1000 Hz wherein the hopper is activated by a capacitance sensor into the powder trough.

11. The method of claim 1, wherein the API further comprises at most 5% (w/w) of an additive.

12. The method of claim 1, wherein the dosage of the neat API in step (b) is in the range of 0.1 mg to 550 mg.

13. The method of claim 12 wherein the dosing of the neat API in step (b) has relative standard deviation (RSD) of less than 5%.

14. The method of claim 1, wherein the neat API is consolidated in the bottom part of the pharmaceutical carrier by vibration, shaking or tapping prior to step (c).

15. The method of claim 1 wherein the method is a continuous process.

* * * * *